United States Patent [19]

Joyeux et al.

[11] Patent Number: 5,753,697
[45] Date of Patent: May 19, 1998

[54] METHOD AND PHARMACEUTICAL COMPOSITIONS CONTAINING ROSMANOL DERIVATIVES

[75] Inventors: Michel Joyeux, Varangeville; Francois Mortier, Malzeville, both of France

[73] Assignee: Laboratoires Dolisos, Paris, France

[21] Appl. No.: 578,682

[22] PCT Filed: Jun. 29, 1994

[86] PCT No.: PCT/FR94/00793

§ 371 Date: Dec. 29, 1995

§ 102(e) Date: Dec. 29, 1995

[87] PCT Pub. No.: WO95/01174

PCT Pub. Date: Jan. 12, 1995

[30] Foreign Application Priority Data

Jun. 30, 1993 [FR] France .................................. 93/07983

[51] Int. Cl.$^6$ ...................................................... A61K 31/27
[52] U.S. Cl. ................................................ 514/486; 514/893
[58] Field of Search ..................................... 514/486, 893

[56] References Cited

FOREIGN PATENT DOCUMENTS 84-185215  6/1984  European Pat. Off. .
85-207789  7/1985  European Pat. Off. .

OTHER PUBLICATIONS

M. Pukl et al., "Inhibitory Effect of Carnosolic Acid on HIV-1 Protease", *Planta Med.*, vol. 58, No. 7, 1992, p. A632.

N. Nakatani et al., "Two Antioxidative Diterpenes from Rosemary (*Rosmarinus officinalis L.*) and a Revised Structure for Rosmanol", *Agricultural and Biological Chemistry*, vol. 49, No. 8, 1984, pp. 2081–2085.

R. Inatani et al., "Antioxidative Effect of the Constituents of Rosem (*Rosmarinus officinalis L.*) and Their Derivatives"*Agricultural and Biological Chemistry*, vol. 47, No. 3, 1983, pp. 521–528.

K. Schwarz et al., "Antioxidative constituents of *Rosmarinus officinalis* and *Salvia officinalis*", pp.95–98.

*Primary Examiner*—Kimberly Jordan
*Attorney, Agent, or Firm*—Young & Thompson

[57] ABSTRACT

Novel pharmaceutical compositions containing an active substance of formula (I), wherein $R_1$, $R_2$ and $R_3$, which are the same or different are H, $CH_3$ or $C_2H_5$. The compositions have useful antiradical and/or antilipoperoxidative and/or hepatotropic properties.

25 Claims, No Drawings

METHOD AND PHARMACEUTICAL COMPOSITIONS CONTAINING ROSMANOL DERIVATIVES

This application is a 371 of PCT/FR94/00793, filed Jun. 29, 1994.

FIELD OF THE INVENTION

The invention relates to antiradical and/or antilipoperoxidative and/or hepatotropic pharmaceutical compositions.

BACKGROUND OF THE INVENTION

In our part of the world, hepatic diseases are dominated by two main aetiological groups:
hepatic pathologies of an infectious nature,
hepatic pathologies of a toxic nature.

Their clinical, biological or histological expressions are often similar, if not identical, however, which poses problems of differential diagnosis.

These aetiological distinctions are not found in most of the traditional pharmacopocias concerned with hepatic disorders where the uses of plant extracts are justified in rather vague terms such as "indicated for hepatic diseases", which may cover an extremely wide variety of pathologies.

There is, moreover, a difference in opinion between what is termed traditional medicine and what is termed modern medicine. The former, despite its lack of semeiological rigour, proposes a plethora of remedies. Numerous plant extracts are used empirically in monotherapy or in association by traditional practitioners. Several hundred plants are thus "indicated for hepatic diseases". The latter, despite what is often very precise knowledge of morbid mechanisms and the existence of etiological classifications that are sometimes very subtle, proposes only a modest range of treatments.

The therapeutic indications of *Rosmarinus officinalis* are numerous and use the various parts of the plant. In particular, diuretic, antiseptic, antirheumatic, healing, astringent, and emmenagogic properties have been found. Above all, *Rosmarinus officinalis* has a privileged place in the field of hepatobiliary diseases. *Rosmarinus officinalis* is composed of numerous active principles. Its action on the liver (cholagogic and cholesteric) is associated mainly with the presence of rosmarinic acid.

Rosmanol is a compound of the group of diterpene lactones and which has been isolated from *Rosmarinus officinalis* (Inatani et al., 1982: "Structure of the new antioxydative phenolic diterpene isolated from Rosmary", Agric. Biol. Chem., 46, 1661 et seq.). Rosmanol is known to have an antioxidant activity (in various non-biological tests), which can give rise to applications as antioxidants in foods (oxidation test on "bacon rashers").

Rosmanol has also be isolated from *Salvia canariensis* and its structure has been determined fully by chemical analysis and by X-ray diffraction (Fraga. et al., 1985: "A revised structure for the diterpene rosmanol", Phytochemistry, Vol. 24, No. 8, 1853–1854).

Rosmanol and 7-ethoxyrosmanol have also been extracted from *Rosmarinus officinalis* (Studies on Medicinal Plants in Paraguay; Studies on "Romero"; Part 1; T. Hayashi, Planta medica 1987; vol. 53, p 394).

This article points out that rosmanol has an inhibiting effect on urease, but no correlation was established in a certain and unambiguous manner with the use of a therapeutic method of treatment.

Moreover, to this day, no link has been made between the pharmacological properties, particularly the hepatoprotective properties of *Rosmarinus officinalis* and the active substance responsible for said properties.

SUMMARY OF THE INVENTION

The invention has made it possible to reveal the chemical compound found to be responsible for the antiradical, antilipoperoxidative and hepatotropic activity of *Rosmarinus officinalis*.

The invention provides novel pharmaceutical compositions, of which the active substance likely to originate from plants, and in particular from *Rosmarinus officinalis*, has been fully identified and may therefore be correctly proportioned.

The object of the invention is a pharmaceutical composition characterised in that it contains, as active substance, at least one of the compounds corresponding to formula I:

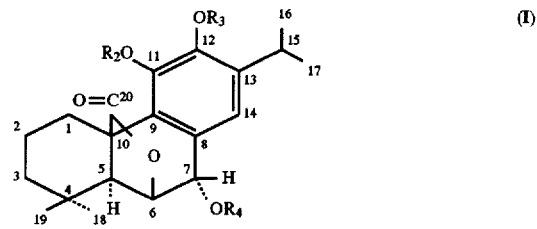

wherein $R_1$, $R_2$, $R_3$, which may be identical or different, represent H, $CH_3$ or $C_2H_5$, possibly in conjunction with a pharmaceutically acceptable salt.

The invention also covers molecules corresponding to formula (I) wherein at least one of the positions that may be substituted (particularly positions 15 and/or 16, and/or 17, and/or 18, and/or 19) may be substituted by substituents such that the molecules retain their antiradical and/or antilipoperoxidative and/or hepatotropic properties, said molecules being equivalents of compounds corresponding to formula I.

The compounds corresponding to formula I have antiradical and antilipoperoxidative activities.

In *Rosniarinus officinalis*, said compounds also have a hepatoprotective action resulting from the association with other active principles of rosemary.

According to an advantageous embodiment of the invention, the pharmaceutical compositions contain as active substance the compound corresponding to formula II:

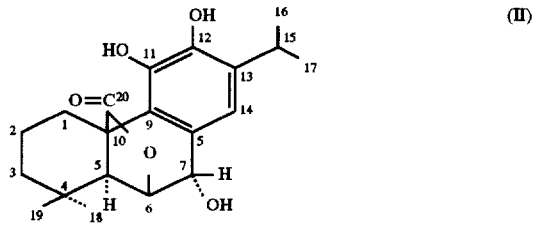

This compound is rosmanol.

Another advantageous group of pharmaceutical compositions according to the invention contains as active substance the compound corresponding to formula III:

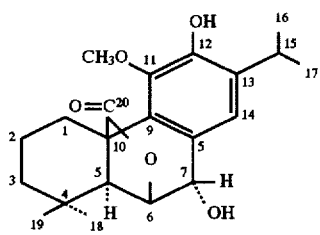

This compound is 11-methoxyrosmanol.

Another advantageous group of pharmaceutical compositions according to the invention contains as active substance the compound corresponding to formula IV:

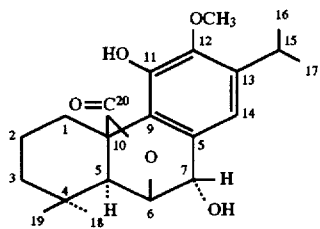

This compound is 12-methoxyrosmanol.

Another advantageous group of pharmaceutical compositions according to the invention contains as active substance the compound corresponding to formula V:

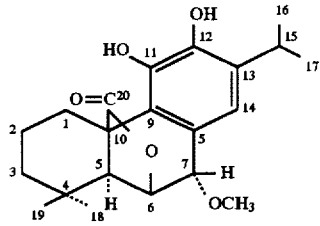

This compound is 7-methoxyrosmanol.

Another advantageous group of pharmaceutical compositions according to the invention contains as active substance a compound corresponding to formula VI:

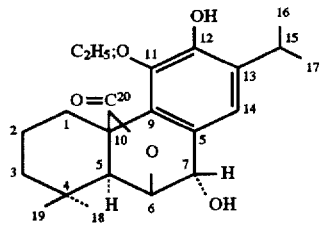

This compound is 11-ethoxyrosmanol.

Another advantageous group of pharmaceutical compositions according to the invention contains as active substance a compound corresponding to the formula VII:

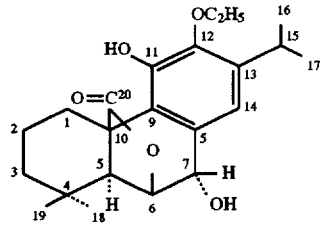

This compound is 12-ethoxyrosmanol.

Another advantageous group of pharmaceutical compositions according to the invention contains as active substance a compound corresponding to formula VIII:

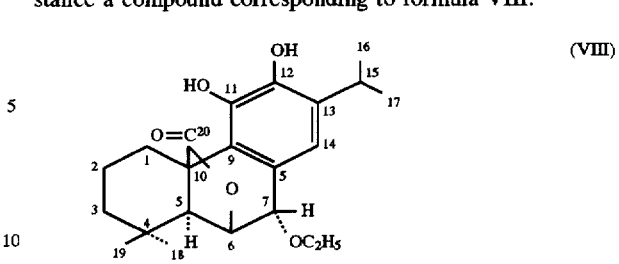

This compound is 7-ethoxyrosmanol.

The invention provides pharmaceutical compositions having antiradical and/or antilipoperoxidative and/or hepatotropic properties containing, as active substance, at least one of the compounds corresponding to formula I.

According to another advantageous embodiment, the invention provides pharmaceutical compositions having antiradical and/or antilipoperoxidative and/or hepatotropic properties containing, as active substance, at least one of the compounds corresponding to formula II, III, IV, V, VI, VII or VIII.

According to another advantageous embodiment, the invention provides pharmaceutical compositions having antiradical and/or antilipoperoxidative and/or hepatotropic properties containing, as active substance, at least one of the compounds corresponding to formula II, V or VIII.

The invention also provides a pharmaceutical composition characterised in that it contains about 0.1 mg/kg to about 100 mg/kg of active substance composed of at least one of the compounds corresponding to formula I, and in particular, about 1 mg/kg to about 10 mg/kg of active substance.

The term "mg/kg" corresponds to mg of active substance per kilogramme of body weight.

The invention also provides a pharmaceutical composition characterised in that it contains about 0.1 mg/kg to about 100 mg/kg of active substance composed of at least one of the compounds corresponding to formula II, III, IV, V, VI, VII or VIII, and in particular about 1 mg/kg to about 10 mg/kg of active substance.

The invention also provides a pharmaceutical composition characterised in that it contains about 0.1 mg/kg to about 100 mg/kg of active substance composed of at least one of the compounds corresponding to formula II, V or VIII, and in particular about 1 mg/kg to about 10 mg/kg of active substance.

Advantageously, the daily dose of active substance is about 2 to about 30 mg/kg and in particular about 3 to about 20 mg/kg.

The pharmaceutical compositions of the invention are characterised in that they are present in an appropriate form for oral, parenteral, rectal or topical administration.

The forms that may be mentioned in particular are tablets, dragees, hard and soft capsules, powders, granules, suspensions or syrups for oral administration, suppositories for rectal administration, sterile or sterilisable solutions for parenteral administration and eyewashes or creams for topical administration.

The compounds of the invention corresponding to formula II, III, IV, V, VI, VII or VIII may be extracted from *Rosmarinus officinalis*.

Rosmanol may be prepared according to the process described for example by T. Hayashi et al. in "Studies on Medicinal Plants in Paraguay: Studies on Romero"; Part 1, Planta medica 1987, vol. 53, p 394.

7-Methoxyrosmanol may be prepared according to the process described by Munehisa Arisawa et al. in "Chemical and Pharmaceutical Studies on Medicinal Plants in Paraguay: Studies on "Romero", Part 2", Journal of Natural Products, Vol. 50, no. 6 pp 1164–1166, Nov. Dec. 1987.

7-Ethoxyrosmanol may be prepared according to the process described by T. Hayashi et al. in "Studies on Medicinal Plants in Paraguay: Studies on Romero"; Part 1, Planta medica 1987, vol. 53, p 394.

The compounds corresponding to formula III, IV or V may also be obtained from compounds corresponding to formula II which have undergone methylation under suitable conditions according to, for example, methods conventionally used for the determination of diterpene or triterpene compounds by gas chromatography.

The compounds corresponding to formula VI, VII or VIII may be obtained from the compound corresponding to formula II, which has undergone ethylation under suitable conditions.

The object of the invention is the use of at least one of the compounds corresponding to formula I and in particular formula II, III, IV, V, VI, VII or VIII defined above for the preparation of a medicinal product intended for the treatment of pathologies associated with mechanisms of free radical formation, or for the treatment of pathologies associated with a lipid peroxidation mechanism, or for the treatment or protection of hepatic cells.

The object of the invention is the use of the compound corresponding to formula II defined above for the preparation of a medicinal product intended for the treatment of pathologies associated with mechanisms of free radical formation, or for the treatment of pathologies associated with a lipid peroxidation mechanism, or for the treatment or protection of hepatic cells.

The object of the invention is the use of the compound corresponding to formula V defined above for the preparation of a medicinal product intended for the treatment of pathologies associated with mechanisms of free radical formation, or for the treatment of pathologies associated with a lipid peroxidation mechanism, or for the treatment or protection of hepatic cells.

The object of the invention is the use of the compound corresponding to formula VIII defined above for the preparation of a medicinal product intended for the treatment of pathologies associated with mechanisms of free radical formation, or for the treatment of pathologies associated with a lipid peroxidation mechanism, or for the treatment or protection of hepatic cells.

According to an advantageous embodiment, the invention relates to the use of compounds corresponding to formula I for the preparation of a medicinal product intended for pathologies associated with a mechanism of lipid peroxidation. This is the case in particular with the treatment of revascularisation problems, for example, in the context of cerebral vascular accidents or in the context of infarction; it is also the case with the treatment of arteritis.

EXAMPLE

EXTRACTION OF ROSMANOL AND METHYLROSMANOL AND DETERMINATION OF THEIR PHARMACOLOGICAL ACTIVITY

A) SELECTION OF ROSMARINUS OFFICINALIS

During the course of this research, 26 plant species were studied. Whenever possible, each of these was identified rapidly by thin layer chromatography.

For each plant extract, the antiradical activity is analysed by means of the diphenyl picrylhydrazyl radical colour loss test as specified below. The extracts are divided into two categories according to whether the colour obtained is less than or more than 50% of that of the reference. The study of the antilipoperoxidative and antinecrotic activity is carried out using the model of isolated hepatocytes poisoned with tert.-butyl hydroperoxide, the methodology of which has been described previously. The experimental doses are always in mg of dry plants.

Apart from plant species traditionally used for their hepatotropic virtues, other plants whose traditional indications are unknown in the hepatobiliary field are also tested in order to assess the pertinence of the pharmacological models adopted.

The traditionally hepatotropic plant species studied during the course of this research are 17 in number, namely:
*Rosmarinus officinalis*
*Cuscuta americana*
*Curcuma domestica*
*Terminalia catappa*
*Tamarindus indica*
*Kalanchoe crenata*
*Staudia gabonensis*
*Cochlospermum tinctorium*
*Eupatorium cannabinum*
*Euphorbia hirta*
*Juniperus communis*
*Crepis rueppelli*
*Pulicaria orientalis*
*Bidens pilosa*
*Carthamus tinctorium*
*Peumus boldus*
*Cochlospermum planchonii*

The other plant species are 9 in number, namely:
*Momordica charantia*
*Justicia pectoralis*
*Annona muricata*
*Eupatorium xanthoxylordes*
*Eschscholzia californica*
*Vaccinium myrtillus*
*Annona reticulata*
*Capparis spinosa*

To do this, two study models were adapted to the use of the above plant species:

a non-biological test, the diphenyl picrylhydrazyl radical (DPPH) colour loss test, a biological test using isolated hepatocytes kept in suspension.

DPPH test

The antiradical activity of the substances tested can be assessed with the aid of this non-biological model. Of all the methods that may be used for this study, we considered the loss of colour of the diphenyl picrylhydrazyl radical (Deby and coll., 1970, Relationship between the essential fatty acids and the levels of tissue antioxidants in mice. C. R. Soc. Biol., 164, 2675–2681) to be the most suitable method for screening because of its speed, ease of use and reasonable cost.

The diphenyl picrylhydrazyl radical is a free radical which is stable under certain conditions, and has an intense violet colour in solution with a maximum absorption at 517 nm. This colour disappears when the electron shells are saturated, i.e. during a change to a non-radical form. As a result, the reduction in the optical density of the solution reflects the power of the substance added to scavenge free radicals. The degree of inhibition is expressed in relation to a reference treated under the same conditions.

The model applied so far to pure molecules has had to be adapted to the study of plant extracts by defining study concentrations. It was thus possible to establish that solutions of plant extracts containing 0.25 to 0.125 g/l allow the entire range of colour loss from 0 to 100% to be covered, depending on the extracts considered. In the absence of any bibliographic support, the criterion of efficiency was initially defined arbitrarily at 50% colour loss, since the predictive value of the results obtained from this test is subsequently refined by comparison with the results of the biological test on isolated hepatocytes.

Test on isolated hepatocytes

The second study model is a biological model based on freshly isolated rat hepatocytes kept in suspension. It permits an approximation of the antilipoperoxidative power of the plant extracts by determination of one of the end products of lipid peroxidation, malonaldehyde (MAD) and an approximation of their antinecrotic power by quantification of the extracellular salting-out of lactate dehydrogenase (LDH) and of aspartate aminotransferase (ASAT), conventional biological markers of cytolysis.

Numerous items of research have shown that the model of isolated hepatocytes in suspension kept alive for short periods of less than a few hours is able to preserve an essential part of the integrity and quality of the hepatic cell, allowing its use in the study of various biochemical or toxicological mechanisms (Klaasen and Stacey, 1982, 147–180, "Toxicology of the liver" PLAA G. L. & Hewitt W. R., Raven Press, New York; Krack and coll., 1983: "Metabolic competence of isolated hepatocytes in suspension. A new tool for in vitro toxicological evaluation", 391–398, Isolation, characterisation and use of hepatocytes, Harris R. A. & Cornell N. W. (eds): Arvis, 1989: "Use of hepatocytes in culture for the toxico-pharmacological screening of natural hepatotropic substances", 236 p., Science Doctorate of the University of Metz, Metz).

Materials and methods

1) Choice of toxicant

Tert-butyl hydroperoxide (tBH) and hepatocytes

Tert-butyl hydroperoxide [$(CH_3)_3COOH$] is an organic hydroperoxide with a molecular weight of 90.1 which may be used for studying oxidative mechanisms. It leads to lipid peroxidation of hepatocytes, the formation of covalent bonds on the cell macromolecules, and to interference with calcium homeostasis.

II) Preparation of hepatocytes in suspension

1. Isolation of hepatocytes 1.1 Animals

Male Sprague-Dawley rats (Iffa Credo, l'Arbresle), 200 to 250 grammes, fed (M25C Extralabo croquettes) and watered ad libitum. The animals are kept in macrolon cages and in a programmed (12 hours light/12 hours darkness) and thermostated ($21°\pm 1°$ C.) animal house.

1.2 Materials

The products used were as follows: collagenase (Sigma), minimum Eagle medium (Flow Laboratory), tert-butyl hydroperoxide (Sigma), Hepes (Sigma), trichloroacetic acid (Prolabo), 2-thiobarbituric acid (Prolabo), dimethylsulphoxide (Prolabo), LDH kit Opt. (Boehringer), GOT kit Opt. (Boehringer).

1.3 Method of isolating hepatocytes

The animal is anaesthetised with pentobarbitone sodium (Clin Midy) in a dose of 60 mg/kg, IP, then heparin is administered in a quantity of 1 ml/kl (heparin 50 Fournier 5000 UI) by the same injection route, and the animal is placed in a dorsal decubitus position in a vessel thermostated to $37°\pm 1°$ C.

After laparotomy and excision of the abdominal wall, a catheter (Critikon 18 G) is placed in the hepatic portal vein. The inferior vena cava is sectioned beneath the renal veins and the liver is perfused at a rate of 30 ml/minute with a phosphate buffer, pH 7.4, using a peristaltic pump (Masterflex). During this phase of lavage, after thoracotomy, a second catheter is inserted through the auricle into the superior vena cava to allow the introduction of the device which recirculates the perfusion medium. When lavage is considered to be correct, the liver is perfused with the aid of a 0.05% p/v solution of collagenase and 5 mM $CaCl_2$ at a rate of 20 ml/min. When the dissociating effect of the enzyme is considered sufficient, the liver is excised then placed in a Petri dish. Glisson's capsule is carefully removed and the cells are brought into suspension by gentle agitation. The connective tissue and the arterio-venous system and the non-dissociated cell clusters are removed by filtration over a silk screen ($68\mu$).

Two decantation-washing operations are then carried out, the residue being brought into suspension in a minimum Eagle medium (MEM) buffered with 20 mM of Hepes. The count is carried out on a Malassez cell. The viability is assessed by the Trypan blue exclusion test. The yield is of the order of 3 to 5. $10^8$ cells and the initial viability must be more than 90%.

1.4 Experiment protocol

The concentration of the hepatocyte suspension is adjusted to 1 million cells per ml of nutrient medium. 4 ml Aliquots of suspension are distributed in 25 ml Erlenmeyer flasks covered with parafilm, kept at $37°$ C. in a water bath with agitation (60 oscillations/min); each sample is suffused individually with a mixture of $O_2/CO_2$ gas (95%/5%). The various toxicants used are added to the culture medium directly or after solubilisation in dimethylsulphoxide (DMSO). The final DMSO concentration is 0.5% v/v. The conditions of use that apply to each toxicant are described in the paragraphs relating thereto. The plant extracts are added directly to the suspension medium in a volume of 20 µl to obtain the final desired concentration (1 mg or 0.5 mg/ml of suspension). The doses are expressed in mg of dry plant per ml of suspension. The determinations are carried out after 30 minutes' incubation.

1.5 Biochemical determinations

Lipid peroxidation is expressed in terms of malonaldehyde (MAD), determined by the 2-thiobarbituric acid method (Bernheim and coll., 1948: "The reaction between thiobarbituric acid and the oxidation products of certain lipids", J. Biol. Chem. 174, 257–264). 1 ml of hepatocyte suspension is mixed with 2 ml of 10% trichloroacetic acid. After being left to stand for 10 minutes, the tubes are centrifuged. 1 ml of supernatent is added to 1 ml of 1% thiobarbituric acid. The tubes are then placed in the water bath at $100°$ C. for 10 minutes then cooled before a reading is taken at 535 nm. The results are given in nMoles/$10^6$ cells.

LDH and ASAT enzyme release is determined by a kinetic enzyme method using Boehringer kits and the results are expressed in mUI/$10^6$ cells. The readings are taken with a spectrophotometer (Uvikon 810, Kontron) under UV light at 340 nm and at $25°$ C.

III) Preparation of the plants

The dry drugs (plants) are bruised roughly then thrown into distilled boiling water in a quantity of 60 g of dry plant per 600 ml of water. The preparation is then placed in an oven at $37°$ C. for 4 hours. The extracts thus obtained are filtered over a Büchner, then concentrated under reduced pressure at a temperature of $40°$ C. They can be kept under good conditions by freeze-drying (freeze-drier CD 52-1, Heto, Denmark). The yield expressed as a percentage represents the ratio of the quantity of freeze-dried product obtained to the quantity, in terms of dry weight, of plant matter used. All the doses mentioned in the screening tests are expressed in mg of dry plants.

1 Chemical identification

The various experimental procedures used during chemical identification are those described by Weniger (1984: "Popular medicine in the central plateau of Haiti", Science Doctorate of the University of Metz, Metz).

A test for the following was carried out on each plant:
alkaloids
flavone compounds
saponisides
tannins
steroid or terpene derivatives.

2 Test for steroid or terpene derivatives 1 g of drug is macerated in 20 ml of ethyl ether in a stoppered Erlenmeyer flask for 24 hours. A few drops of the maceraresidue is dissolved in watchglass and the residue is dissolved in 2 drops of acetic anhydride. A colour turning from green to mauve after the addition of one drop of $H_2SO_4$ suggests the probable presence of steroid and/or terpene derivatives.

RESULTS

Of the 26 plants tested, Rosmarinus officinalis gives the first results as follows:

Test for inhibition of the DPPH radical:

Tested under the conditions described above, the aqueous extract of Rosmaninus officinalis gives rise to 84% colour loss for a solution of 0.25 g/l and 65% for a solution of 0.125 g/l. In view of these results, Rosmatinus officinalis is classed as type II (% colour loss >50%).

Test on isolated hepatocytes:

The experiment is performed according to the protocol described previously. Rosmarinus officinalis has a protective effect with regard to lipid peroxidation and necrotic effects brought about by tert-butyl hydroperoxide. Rosmatinus officinalis (0.5 and 1 mg of dry plant/ml of hepatocyte suspension) inhibits in a very significant manner enzyme salting-out and the production of malonaldehyde, confirming the advantage of this model in the treatment of hepatic diseases of toxic origin. The aqueous extract of young shoots of Rosmarinus officinalis is presented in the following tests as a positive reference product.

B) STUDY OF ROSMARINUS OFFICINALIS

1 Study of a delayed addition of Rosmarinus officinalis

After verification that R. officinalis had no effect on the methods of measurement used, and before commencing the fractionation phase, efforts were made to remove the possibility of any potential extracellular interaction between the toxicant and the plant extract with the aid of a delayed addition of the extract 10 minutes after poisoning with tBH. This period was considered to be sufficient for the various factors of cell necrosis to take effect. The results obtained during such experiments show that the protective effect appears despite the delayed addition; the protective effects are therefore of an intracellular nature.

II Effect of the extraction solvent

During the screening phase, the extractions were carried out using the solvent most often found in traditional preparations: water. Before commencing the fractionation phase of Rosmarinus officinalis, a series of differential extractions with a Soxhlet were carried out using solvents of increasing polarity according to the sequence chloroform, ethyl acetate, ethanol, water in order to find the most efficient extraction solvent. All the fractionation work was carried out on young shoots (just after the buds opened) of rosemary. On receipt of the plants, 24 hours later, the young shoots (terminal parts 2 to 3 cm long, tender green) are separated from the rest of the aerial part and frozen at −20° C.

II-1 Soxhlet 1

II-1 1 Procedure

A first Soxhlet extraction (Soxhlet I) is carried out with 80 g of young rosemary shoots, defrosted and well bruised before being placed in the Soxhlet thimble. Each leaching is carried out with 600 ml of solvent until said solvent emerges completely colourless from the thimble. The extracts obtained are then concentrated under vacuum then frozen before being freeze-dried. The quantities of freeze-dried products obtained are as follows:

1.73 g for the extraction with chloroform
0.24 g for the extraction with ethyl acetate
2.36 g for the extraction with ethanol
1.94 g for the aqueous extraction (80 g of fresh plant give 30.08 g of dry plant).

When brought back to ambient temperature, the chloroformic extract separates into a lower liquid phase and an upper solid, waxy phase. The latter, probably originating from the cuticle of the young shoots, is separated by filtration, dried in the air and stored separately. After filtration, the liquid part is treated like the other extracts by freeze-drying.

II-1-2 Pharmacological control

The experimental results obtained from the four freeze-dried products on isolated hepatocytes after poisoning with tert-butyl hydroperoxide (1.5 mM) show that poisoning is evident both as regards the production of malonaldehyde and enzyme salting-out. Two extracts, the one with ethyl acetate and the one with ethanol, do not exhibit any pharmacological action on this model. The aqueous extract reduces enzyme release but, unlike an aqueous extract obtained by infusion/ maceration, has no effect on the formation of MAD. The chloroformic extract completely inhibits the release of lactate dehydrogenase and reduces the production of MAD in a highly significant manner. The chloroformic extract in a dose of 1 mg of dry plant per ml of hepatocyte suspension exhibits a greater activity than all the aqueous extracts tested during the preliminary screening operation.

II-2 Soxhlet II

II-2-1 Procedure

In view of these results, a second differential Soxhlet extraction (Soxhlet II) is carried out starting from 120 g of young defrosted shoots of Rosmarinus officinalis, using two extraction solvents in succession, chloroform then water. The method of preparing the freeze-dried products is identical to that described above. The quantities of freeze-dried products obtained are as follows:

3.91 g for the chloroformic extract
7.23 g for the aqueous extract

II-2-2 Pharmacological control

The results of the experiments carried out on these new extracts (not shown) confirm the previous work. The chloroformic extract tested in a dose of 1 mg of dry plant per ml of suspension reveals a considerable activity, whilst the extract corresponding to the aqueous Soxhlet extract has no effect on the parameters studied.

II-3 Chromatographic characterisations

Thin layer chromatography profiles are then produced for the various freeze-dried products obtained (Soxhlet I and Soxhlet II) with a view to testing for reducing compounds, flavonoids and phenolic acids, since these substances are likely to be responsible for the activity, according to certain authors. Tests for triterpenes, compounds extracted by weakly polar solvents and possibly also involved in the hepatoprotective effects (Hikino and coll., 1984: "Antihepatotoxic actions of papyriogenins and papyriosides, triterpenoids of Tetrapanax papyriferum leaves", J. Ethnopharmacol. 12, 231–235) are also performed.

For the requirements of the invention, only the tests for triterpenes will be detailed below.

II-3-1 Test for triperpenes on Soxhlet I and Soxhlet II

The test for triterpenes is performed on a Kieselgel G60 silica gel plate without fluorescence (20×20; Merck). The solvent system is composed of a mixture of benzene/acetic acid in the proportions 99/1 (v/v). Migration is halted when the solvent is approximately 3 cm from the upper edge of the plate. After drying, a 20% (m/v) chloroformic solution of antimony trichloride is sprayed onto the plates. The plates are placed in the oven at 120° C. for 15' then observed under ultraviolet light at 366 nm.

The extract obtained from the infusion/maceration of young rosemary shoots and the extracts obtained by aqueous leaching carried out during the two differential Soxhlet extractions do not exhibit any spot. The various chloroformic extracts provide the greatest number of spots; moreover, said spots are reproduced identically in these extracts; in particular, the waxy part and the filtrate give similar chromatographic profiles. The extracts obtained with ethyl acetate and ethanol are also identical among themselves.

II-4 Soxhlet III

II-4-1 Procedure

In view of these results, a third Soxhlet extraction is carried out (Soxhlet III), this time using chloroform followed by methanol. 100 g of fresh defrosted plant are used, the method of preparing the young shoots of R. officinalis remaining the same as those described before. The quantities of freeze-dried products obtained are as follows:

4.2 g for the chloroformic extract 5.6 g for the methanolic extract.

II-4-2 Pharmacological control

The extracts obtained are tested on the in vitro model. Again, the chloroformic extract shows extremely interesting activity, almost completely inhibiting the action of tert-butyl hydroperoxide. The methanolic extract itself is not very active as regards enzyme salting-out and the production of MAD.

II-5 Chromatographic characterisation

I-5-1 Test for triterpenes

The protocol used is the one described above. The chloroformic extracts derived from the two extractions have identical chromatographic profiles (not shown here). The methanolic extraction reveals 2 spots at the bottom of the plate and 1 spot in the upper part; the same profile is obtained with the ethyl acetate and ethanol fractions.

II-6 Conclusions and verifications

All these results clearly reveal:

the superiority of the chloroformic extracts compared with all the other extracts tested, both in terms of the formation of malonaldehyde due to lipid peroxidation and in terms of enzyme salting-out signifying cell necrosis.

the apparent absence, on the basis of data from thin layer chromatography, of flavonoids in the chloroformic extracts and their presence in the extracts without any pharmacological effect. This suggests that they are not responsible for activity in the model studied. From a logical viewpoint, therefore, the pharmacological activity is likely to be attributable to the compounds developed by antimony trichloride, i.e. compounds of a terpene, steroid or carotenoid nature.

These conclusions prompt two remarks:

Certain authors had suspected that the pharmacological activity of rosemary was based on the presence of certain phenolic acids such as caffeic acid, chlorogenic acid and above all rosmarinic acid. These substances, which are insoluble or sparingly soluble in chloroform, are entrained by solvents such as ethanol, methanol or water.

The absence of pharmacological activity of the corresponding extracts caused these pure substances to be tested on the model of isolated hepatocytes poisoned with tert-butyl hydroperoxide.

These compounds are solubilised in DMSO and added in a volume of 20 μl to the hepatocyte suspension (DMSO= 0.5% v/v) such that their final concentration is 100 μM (approx. 15 μg/ml). Rosmarinic acid represents 1 to 3% of rosemary (dry weight) so 1 mg of dry plant/ml corresponds to a weight between 10 and 30 μg of rosmarinic acid/ml of suspension.

Neither caffeic acid nor chlorogenic acid protect the hepatic cell poisoned by tert-butyl hydroperoxide. Rosmarinic acid inhibits the formation of malonaldehyde but has no effect on enzyme salting-out. These substances do not, therefore, seem to be responsible for the protective activity brought about by an extract obtained by infusion/maceration.

If it is considered that substances of a terpene or steroid nature are responsible for the pharmacological activity, two hypotheses need to be verified.

the transfer of this type of substance to the infusion/maceration, a pharmacologically active extract because it is capable of inhibiting the production of MAD and enzyme salting-out brought about by tert-butyl hydroperoxide the existence of a difference in activity between the infusion/maceration and the aqueous Soxhlet extraction after elution with chloroform which will have had the effect of entraining these compounds.

Test for triterpenes in the aqueous and aqueous alcoholic extracts

Procedure 700 mg of freeze-dried product obtained by infusion/maceration of young rosemary shoots at 37° C. for 4 hours are solubilised in distilled water. A liquid-liquid extraction with chloroform is then carried out. Agitation is maintained for one hour. After being left to stand, the two phases are separated, concentrated under vacuum at 40° C. then freeze-dried. The aqueous fraction yields 563.4 mg; the chloroformic fraction yields 92 mg.

An extraction with chloroform (100 ml) was also carried out on 250 ml of mother tincture prepared industrially (Dolisos batch no. 10769, alcoholic str.=6209, 21 days' maceration). Two fractions are separated after being agitated for one hour and left to stand, then concentrated under vacuum.

Chromatographic characterisation

The test for triterpenes is carried out on each fraction obtained according to the method described above. The solvent used for migration is chloroform; the developer is antimony trichloride. The spot corresponding to the Soxhlet extraction with chloroform is 20 times less concentrated than the other spots.

The Soxhlet chloroformic extraction (Soxhlet II) gives the highest number of spots (not shown). The aqueous fractions of the infusion/maceration and of the mother tincture do not give any spot with antimony trichloride. In the case of the chloroformic fractions, on the other hand, four spots are revealed on the bottom of the plate for the fraction derived from the infusion/maceration, and a higher number of spots is obtained for the fraction derived from the mother tincture.

The infusion/maceration at 37° C. for 4 hours is therefore a method of extraction which allows the transfer of relatively nonpolar compounds which are readily extracted with chloroform during a secondary liquid-liquid extraction. The presence of these compounds which are likely to be responsible for the hepatoprotective activity could thus explain the pharmacological activity of the extract produced by infusion/maceration, and their concentration, which is lower than that found in a chloroformic extract, could explain the lower level of protection. The presence of a larger number of spots in the case of the chloroformic fraction of the mother tincture is probably associated with the longer extraction time (21 days).

Comparison of the activity of aqueous extracts depending on the type of extraction The protocol used during the in vitro experiment is the one described above. All the extracts are tested in a quantity of 1 mg of dry plant per ml of suspension. The final concentration of DMSO is 0.5% v/v.

Once again, the results show a greater activity of the chloroformic extract compared with the aqueous extracts, both in terms of inhibition of the peroxidative processes and in terms of necrotic effects. The effect of the aqueous extract derived from the infusion/maceration is greater than that of the extract obtained by Soxhlet extraction.

These results bear out the thesis according to which the hepatotropic activity of rosemary seems to be due to relatively nonpolar compounds.

In the light of these studies, the chloroformic extracts of *Rosmarinus officinalis* appear unequivocally to be the most efficient in terms of hepatoprotection on the experimental model adopted. Fractionation by thin layer preparative chromatography is then carried out on these extracts with a view to obtaining the most complete purification possible of the active principles. It is carried out on the basis of the Soxhlet II chloroformic extract of young shoots of *Rosmaninus officinalis*.

III Fractionation of the chloroformic extract by preparative chromatography

General methodology

The day before the fractionations, glass plates (20×20), clean and degreased, are coated with 0.5 mm of a mixture of Merck G60 silica gel (45 g) and distilled water (90 g) using a Stahl applicator. The plates are dried in the air then oven-dried at 100° C. for 2 hours. The plates are placed in the oven for one hour at 100° C. just before use.

The choice of migration solvent for each new preparative chromatography is guided by the previous migrations; the first solvent used is chloroform. After the solvent has migrated over a distance of 15 cm, the plates are removed then dried in the air. Various migration zones are then identified in order to perform a pharmacological control on which the subsequent fractionations can be based.

III-1 Primary fractionation

III-1-1 Procedure 50 mg of freeze-dried product of the Soxhlet II chloroformic extract are solubilised in 1 ml of chloroform then applied (0.1 ml/cm) to the silica gel plate using a Firmenich applicator. The solvent used is chloroform. After migration, the plates are removed from the tank then dried in the air. One of the plates is used to test for terpene compounds with the aid of a 20% chloroformic solution of antimony trichloride. The other is used to continue fractionation. Six zones (not shown) are obtained in the natural light, and under UV light at 366 nm after the plates have been sprayed with the developer and placed in the oven at 120° C.,:

a spotting zone corresponding to the place where spotting was carried out 4 migration zones a reference zone situated below the spotting zone is also identified.

Each zone is delicately scraped off the glass support and the silica gel is placed in 25 ml Erlenmeyer flasks. Two successive washes with 20 ml of chloroform with magnetic agitation are carried out. After each wash, centrifugation is carried out to separate the supernatant from the silica gel; a third wash is carried out with 20 ml of methanol, a more polar solvent, and after centrifugation the methanolic supernatant is added to the chloroformic supernatants already obtained. Each fraction is then concentrated under vacuum at 40° C. until a volume of 1 to 2 ml is obtained and then poured into a glass haemolysis tube where, after evaporation to dryness, it is kept at ambient temperature under a stream of nitrogen.

III-1-2 Chromatographic characterisation

A chromatographic control is then carried out and compared with that of the initial Soxhlet II chloroformic extract. Two solvent systems are used, chloroform and a solvent with a greater eluting power composed of a mixture of chloroform and methanol in proportions of 95/5. Under UV light, after the plates have been sprayed with antimony trichloride and placed in the oven, the various spots of the initial chloroformic extract are reproduced in zones 1 to 4. The spotting zone and the reference zone do not exhibit any spot with this developer system.

III-1-3 Pharmacological control

The various fractions obtained are then tested on isolated hepatocytes poisoned with tBH (1.5 mM), after being solubilised in DMSO such that the final concentration per ml of hepatocyte suspension corresponds to the quantity of fraction contained in 1 mg of dry plant. The number of fractions identified by chromatography was deliberately restricted so as to allow an assessment of the pharmacological action of the various fractions simultaneously and thus to allow comparison of their activities on cell populations that are homogeneous in all respects. Each experiment is carried out at least twice. The protective effect on cell necrosis is assessed in terms of LDH salting-out, the antilipoperoxidative activity is assessed by the reduction in the MAD formed.

It is also possible to summarise the activity of the zones derived from this first fractionation. The reference zone with no pharmacological effect is not shown on the graphs. The starting chloroformic extract (Soxhlet II) used in a quantity of 1 mg of dry plant per ml of suspension is used as a reference. Enzyme release is very much inhibited by the spotting fractions 1, 2 and 3. Zone 4, the most eluted zone, is inactive. The sensitivity of MAD is greater; in all the experiments, the zones that migrated the least (spotting zone and zone 1) exhibit the greatest activity. Said activity is comparable with that of the reference chloroformic extract. In view of these results, fractionation is continued on the basis of the spotting zone and zone 1.

III-2 Fractionation of the spotting zone

III-2-1 Procedure

The spotting fraction is solubilised in 1 ml of chloroform then applied in a band using a manual applicator to plates prepared according to the protocol described above. The solvent used is a mixture of chloroform and methanol in proportions of 90/10 v/v so as to increase the eluting power with respect to the previous separation. Migration is halted when the solvent front has travelled 15 cm, the plate is then dried and observed in natural light. As before, five zones are identified, certain zones combining several bands (not shown). These zones numbered D1 to D5, from the bottom to the top of the plate, are scraped off their glass support, placed in Erlenmeyer flasks and washed twice with chloroform and then once with methanol according to the conditions described above. After being concentrated under vacuum, the fractions are then placed in haemolysis tubes and evaporated to dryness.

III-2-2 Pharmacological control

Experimental controls are carried out on isolated hepatocytes poisoned with tert-butyl hydroperoxide. The starting extract (spotting zone) is tested simultaneously to serve as a reference. The activity with regard to the peroxidative effects and necrotic effects is reproduced for the spotting reference. On the other hand, the various fractions do not exhibit any pharmacological activity. The attempt to purify this fraction is halted at this stage.

III-3 Fractionation of zone 1

III-3-1 Procedure

The zone 1 fraction is solubilised in 1 ml of chloroform before being applied according to the protocol described above. The solvent used is a solution of chloroform and methanol (90/10). As with the spotting zone, five zones are identified (not shown), some zones combining several bands. These zones are numbered from 1.1 to 1.5 from the bottom to the top of the plate, scraped off, washed twice with chloroform and then once with methanol. The fractions are concentrated under vacuum, then evaporated to dryness in haemolysis tubes.

III-3-2 Pharmacological control

The in vitro tests carried out on these fractions show that zones 1.3 and 1.4 retain considerable activity. These fractions are in turn purified by thin layer preparative chromatography.

III-4 Fractionation of zone 1.3

III-4-1 Procedure

After solubilisation of fraction 1.3, the protocol used is identical to those described above. The migration solvent contains 85% of chloroform and 15% of methanol so as to increase the eluting power. After migration and drying, 9 zones are identified, numbered from 1.3.1 to 1.3.9 from the bottom to the top of the plate (not shown). Each zone is scraped off then washed with chloroform and methanol, the supernatants are concentrated under vacuum and evaporated to dryness according to the conditions already described.

III-4-2 Pharmacological control

The pharmacological activity both with respect to MAD and to LDH (not shown) is reproduced clearly for starting fraction 1.3 acting as a reference. On the other hand, purification diluted the activity such that no fraction exhibits a particular pharmacological effect. The attempt to purify these fractions is naturally halted at this stage.

III-5 Fractionation of zone 1.4

III-5-1 Procedure

Fraction 1.4 is solubilised in 1 ml of chloroform and applied to a plate according to the usual procedure. In view of the position of zone 1.4 during the previous separation, a less eluting solvent composed of a mixture of chloroform and ethyl acetate (85/15 v/v) is used. When the solvent has travelled 15 cm, the plate is removed and dried. After drying, it is noted that the lower half of the migration zone is ochre in colour and no clearly identified band appears there. A second migration is carried out as far as the first band visible during the first migration (not shown) using a chloroform/methanol mixture (90/10 v/v).

After drying, the plate is divided into six zones numbered 1.4.1 to 1.4.6 from bottom to top. Each of these zones is then washed and the solvents removed by the procedure already described.

III-5-2 Pharmacological control

In order to be tested experimentally, each of the zones is absorbed by DMSO so that the final quantity/ml of hepatocyte suspension corresponds to 1 mg of dry plant. The starting fraction 1.4 acts as a reference; it inhibits the peroxidative and necrotic effects brought about by tert-butyl hydroperoxide in a highly significant manner (not shown). Fraction 1.4.2 remains very active, particularly as regards enzyme salting-out. Fraction 1.4.3 exhibits less activity, the four other fractions are ineffective. In view of the small quantity of fraction 1.4.2, purification is halted at this stage and a decision is made to attempt to identify the components of this fraction.

IV Identification of fraction 1.4.2

IV-1 Thin layer chromatography on fraction 1.4.2

IV-1-1 Identification of fraction 1.4.2 by antimony trichloride

Fraction 1.4.2 is spotted on a plate coated with Merck Kieselgel G60 silica gel. Ursolic acid, oleanolic acid, α amyrin and β amyrin are used as references. These substances, which have already been isolated in the aerial parts of *R. officinalis*, are capable of being extracted by the solvent systems used. The migration solvent is a mixture of chloroform and methanol in proportions of 90/10. The developer is a 20% solution of antimony trichloride in chloroform. The reading is taken at 366 nm after oven-drying at 120° C. for 10'. Ursolic acid, oleanolic acid, α amyrin give yellowish spots (not shown). The spot of β amyrin situated at the same level as that of α amyrin is more orange. Fraction 1.4.2 gives a spot situated at the level of those of oleanolic and ursolic acid but has a more ochre colour.

IV-1-2 Identification of fraction 1.4.2 by cerium sulphate

The support, references, and migration solvent are identical to those described in the previous paragraph. The developer is a mixture of cerium sulphate and sulphuric acid (d=1.84) and tests for any derivatives of tocopherol. The same spots of an orange colour are reproduced for ursolic acid, oleanolic acid, α amyrin and fraction 1.4.2; β amyrin exhibits a grey-green colour (not shown). No additional spot is revealed by this method compared with those visualised after spraying with antimony trichloride.

IV-1-3 Identification of fraction 1.4.2 by anisaldehyde

Spotting is carried out on a plate coated with Merck Kieselgel G60 silica gel. α and β Amyrin, ursolic and oleanolic acids and the Soxhlet II chloroformic extract are used as references. After migration, the plate is sprayed with the following developer:

| | |
|---|---|
| methanol | 85 |
| glacial acetic acid | 10 |
| 95% sulphuric acid | 5 |
| anisaldehyde | 0.5 |

Two solvent systems are used for the migrations.

A chloroform-methanol system (90/10) already used before allows the spots described before to be reproduced (not shown): α and β amyrin close to the solvent front with an ochre colour, oleanolic acid (violet spot) and ursolic acid (grey spot) a little lower. The Soxhlet II chloroformic extract naturally gives the highest number of spots. Fraction 1.4.2 gives a single visible spot with a grey-violet colour and an Rf close to that of oleanolic and ursolic acids.

A toluene-ethyl acetate system (95/5) is used in an attempt to visualise the possible presence of more nonpolar compounds in fraction 1.4.2. The references remain the same as before. The profile obtained is not shown. A large number of spots, corresponding to the most nonpolar compounds of the Soxhlet II chloroformic extract, are indeed reproduced. The other references are situated in the lower half of the plate, as is the spot of fraction 1.4.2, so this migration solvent is not able to visualise new spots for this fraction.

In view of all these results, it seems that the pharmacologically active fraction 1.4.2 seems to be relatively well purified. A single spot appears in TLC after spraying the developers likely to reveal compounds found in the starting chloroformic extract, notably compounds of a terpene or steroid nature. The only spot revealed is situated in a zone close to that of the spots of ursolic and oleanolic acid, which are known to be present in rosemary and which certain authors had considered to have potential pharmacological activity. In order to verify the presence of these compounds in fraction 1.4.2 and to mitigate the increasingly limited possibilities of investigation of thin layer chromatography techniques on samples in a small quantity, identification of fraction 1.4.2 by gas chromatography combined with mass spectrometry was carried out. At the same time, purification on a plate is carried out after methylation of the very small remaining quantity of fraction 1.4.2.

V-2 Gas chromatography combined with mass spectrometry

In order to increase the volatility of the components of fraction 1.4.2, the derivatives of the latter are prepared by silylation. The addition of the trimethylsilyl group increases the volatility of the compounds with good thermal and chemical stability. The silylation agents used have a relatively wide reactivity which may, in particular, affect R—OH, Ar—OH or R—COOH groups.

Gas chromatography is then carried out. The temperature of the injector is 280° C., that of the column is 220° C.; after an isothermal phase of 5', the temperature is increased at 5° C. per minute.

α and β Amyrin, oleanolic acid, ursolic acid are used as references. The purification of this fraction is satisfactory, less than twenty compounds being found. Of these, two main groups may be distinguished.

A group of three compounds appearing between 8 and 9 minutes (group 1) after injection a group of four compounds appearing later, between 22 and 24 minutes after injection (group 2).

Comparison with the chromatograms of the references and a study of the mass spectra makes it possible to establish:

the absence of a and B amyrin in fraction 1.4.2 the presence of oleanolic acid in fraction 1.4.2 the presence of ursolic acid in fraction 1.4.2.

the group appearing latest includes two other compounds, one of which is very much in the minority and is not identified; the other gives a mass spectrum which suggests a structure very similar to that of ursolic acid.

finally, group 1 comprises three unidentified compounds.

IV-3 Purification of fraction 1.4.2 after methylation

A part of fraction 1.4.2 is then methylated with diazomethane, then separated by another thin layer preparative chromatography (silica gel G 60) using a chloroform/ petroleum ether migration solvent (75/25). Four fractions are identified; the higher fractions (2,3,4) likely to contain terpene substances already identified by the previous GC/MS are set aside. Only fraction 1, corresponding to the spotting zone, is separated again on silica gel using a chloroform/ethyl acetate (90/20 v/v) [sic] eluent system. Two spots are then obtained (1a and 1b). Fraction 1a, obtained in a negligible quantity, has a mass spectrum which does not provide any particular information ; on the other hand, the mass spectrum produced by electron impact starting from zone 1b shows a molecular ion at 342 which may correspond to tetramethylated lutolein (not shown). Fragmentation ions which are characteristic of this compound are also found.

IV-4 Conclusions

In the light of this attempt at fractionation, the only compounds clearly identified as being present in fraction 1.4.2 and, consequently, as being potentially responsible for pharmacological activity, are triterpenes.

A series of experiments was therefore carried out on isolated hepatocytes poisoned with tert-butyl hydroperoxide, in order to assess the effect of the triterpenes identified on the hepatotoxic mechanisms.

V Pharmacological activity of the identified compounds of fraction 1.4.2

V-1 Test for the pharmacological activity of the terpene compounds

During a first experiment, ursolic acid, oleanolic acid and a amyrin are tested in a dose of 100 μM. Quercetin, used in the same dose, acts as a reference substance.

No pharmacological activity is found for oleanolic acid and ursolic acid on the model used, so these compounds are not responsible for the activity of fraction 1.4.2 derived from a chloroformic extract of young shoots of R. officinalis in the experimental model used.

Lutolein, which is present in fraction 1.4.2, could therefore be regarded as possibly responsible for the hepatoprotective effect of young shoots of R. officinalis, in the light of this study. It was necessary, therefore, to assess the quantity of lutolein present in the chloroformic extract and extract 1.4.2 in order to verify whether this quantity was sufficient to cause the pharmacological activity.

It was found that it is present in quantities that are too small in themselves to explain the pharmacological activity.

A fresh attempt at purifying the Soxhlet II chloroformic extract of young shoots of R. officinalis is therefore carried out in order to identify more precisely the compounds responsible for the pharmacological activity. This test uses a different separation method to the previous one and is carried out on a chromatotron.

VI Fractionation of the chloroformic extract of R. officinalis by chromatotron

The chromatotron (Harrison Research 7924T) allows separation by thin layer chromatography accelerated by a centrifugal effect. The solution to be separated is applied near the centre of a disc covered with an absorbent layer and rotating at great speed; elution by the various solvents used takes place from the centre towards the periphery. The migration of the various band may be monitored by illuminating the disc by UV light (254 nm). The plates are produced the day before each manipulation. 45 grammes of Merck Kieselgel 60 PF 254 are mixed with 90 grammes of distilled water. The mixture is spread (in a thickness of 1 mm) with an applicator onto a clean and carefully degreased glass disc, 20 cm in diameter. The discs are dried in the air and then in the oven at 70° C. for 5 hours. On the day of the manipulation, the discs are reactivated by heating in the oven for one hour.

VI-1 Chromatotron I

VI-1-1 Procedure

The first separation is carried out on the basis of 100 mg of freeze-dried product of the Soxhlet II chloroformic extract. Chloroform is the only elution solvent used. Fractionation is stopped when the eluent is colourless and the bands do not evolve any further. The various fractions produced over time are grouped together into four batches (A, B, C, and D) corresponding to a volume of eluent of 75 ml each. The four fractions are concentrated under vacuum at 40° C. until a dry residue is obtained.

VI-1-2 Pharmacological control

In order to be tested pharmacologically, the four fractions are absorbed by DMSO such that the final concentration corresponds to 1 mg of dry plant per ml of hepatocyte suspension. The results (not shown) show the similar behaviour of these four fractions as regards the formation of malonaldehyde and the release of lactate dehydrogenase and aspartate aminotransferase. The pharmacological activity increases with the elution time, the fraction obtained latest being the most active. These results reveal that the active principles of the chloroformic extract of young shoots of rosemary, although completely extracted by the Soxhlet chloroformic extraction (the extracts of greater polarity being inactive) show relatively little affinity for the very nonpolar solvents.

This point was confirmed by performing a liquid-liquid extraction using a mixture of hexane and chloroform (1/1 v/v) on the basis of a freeze-dried Soxhlet II chloroformic extract. The fractions obtained after one hour's agitation are evaporated to dryness then absorbed by DMSO to be tested at a concentration corresponding to 1 mg of dry plant/ml of hepatocyte suspension. The experimental results show clearly that the hexane fraction containing the most nonpolar compounds is not pharmacologically active, the remainder of the chloroformic extract being very active. Chromatographic profiles carried out on the hexane part did not reveal either flavonoids by the NEU reagent (diphenylboryloxyethylamine) or terpene compounds by antimony trichloride.

VI-2 Chromatotron II

VI-2-1 Procedure

A second separation is carried out with 100 mg of freeze-dried Soxhlet II chloroformic extract. Three solvents are used successively, first methanol then ethyl acetate and finally chloroform until the plate is clean. The various fractions produced over time are grouped together to obtain two methanolic fractions (F1, F2) of 75 ml each, and two ethyl acetate fractions (F3, F4) of 75 ml each; all the chloroformic fractions are grouped together (F5).

VI-2-2 Chromatographic characterisations

Tests for terpene and steroid compounds

The protocol used was described above; the solvent used is a mixture of benzene and acetic acid (99/1). The developer is antimony trichloride. The references used are the Soxhlet II and Soxhlet III chloroformic extracts and the Soxhlet III methanolic extract (not shown). The first methanolic fraction (F1) derived from the Soxhlet II chloroformic extract exhibits four of the five spots of the starting extract; the fifth spot situated in the middle of the plate does not appear in any of the fractions. F1 exhibits two spots not found on the Soxhlet III methanolic extract which has no pharmacological effect.

VI-2-3 Pharmacological control

The various fractions (F1 to F5) are absorbed by DMSO such that the final concentration corresponds to 1 mg of dry plant/ml of suspension. The pharmacological activity of these fractions on the peroxidative effects and enzyme salting-out is shown. Poisoning is evident as regards the three parameters considered. The first methanolic fraction leads to manifest hepatoprotection, the other extracts are completely ineffective.

VI-3 Chromatotron III

VI-3-1 Procedure

Depending on the previous results, a third separation procedure is carried out with 100 mg of freeze-dried chloroformic extract (Soxhlet II) of young shoots of *R. officinalis*. Initially, four fractions are isolated according to the following procedure:

fraction 1←elution with 75 ml of chloroform fraction 2←elution with additional 75 ml of chloroform fraction 3←elution with 75 ml of methanol fraction 4←elution with 75 ml of a mixture of methanol and acetic acid (95/5 v/v)

After concentration in a rotary evaporator, fraction 3 is fractionated by the chromatron according to the following sequence:

fraction 3.1←elution with 75 ml of a mixture of $CHCl_3$+ $CH_3COOH$ (95/5 v/v)

fraction 3.2←elution with additional 75 ml of a mixture of $CHCl_3$+$CH_3$ COOH (95/5 v/v)

fraction 3.3←elution with 75 ml of methanol

After concentration, fraction 3.3 itself is fractionated by the chromatotron.

fraction 3.3.1←elution with 75 ml of $CHCl_3$ fraction 3.3.2←elution with additional 75 ml of $CHCl_3$ fraction 3.3.1 [sic] ←elution with 75 ml of $CH_3COOH$ VI-3-2 Chromatographic characterisation The test for compounds of a steroid and terpene nature is carried out on the various fractions obtained by TLC (Merck G60 silica gel) using chloroform as migration solvent.

VI-3-3 Pharmacological control

The various fractions are absorbed by DMSO so as to study their antilipoperoxidative and antinecrotic activity. The doses tested are equivalent to 1 mg of dry plants/ml of hepatocyte suspension. The results clearly show that fraction 3.2 is the most effective both in respect of the peroxidative effects and enzyme release signifying cell necrosis.

VI-3-4 Identification of fraction 3.2

Fraction 3.2 is analysed by gas chromatography after silylation. The temperature of the injector is 180° C., the temperature programme of the oven starts at 240° C., remains stable for 1 minute then increases at a rate of 10° C. per minute until 280° C.

Five majority compounds are found (not shown). Their masses range from 279 to 515 (not shown). By comparing the mass spectra of fraction 3.2 with those of the compounds derived from fraction 1.4.2, it is noticed that only one compound is common to both these fractions. Compound A with a mass equal to 504 has, in fact, a mass spectrum that can be superimposed on the one exhibited (not shown). It can thus be concluded that the two fractionation procedures adopted which use different methodologies (chromatotron and preparative TLC) make it possible to isolate the same compound from the most active pharmacological fractions. This compound may thus be regarded as being chiefly responsible for the pharmacological activity (antilipoperoxidative and antihepatotoxic) of *Rosmatinus officinalis*.

VI-3-5 Identification of the compound responsible for the pharmacological activity In view of the procedures used during fractionation and the mass spectra obtained, the hypothesis was put forward that the compound responsible for the hepatotropic activity could belong to the group of triterpene lactones present in rosemary and whose main compounds were originally isolated from *Salvia officinalis*. These compounds, chiefly carnosol and rosmanol, exhibit a remarkable antioxidant activity in various non-biological tests used for testing for food antioxidants ("bacon rashers" oxidation test) (Inatani and coll., 1982: "Structure of the new anitoxydative phenolic diterpene isolated from Rosmary" Agric. Biol. Chem., 46, 1661 et seq). The compound having an m/z at 562 of fraction 1.4.2 may correspond to rosmanol. The active principle having an m/z at 504 must correspond to a methylrosmanol, since the presence of the methyl group prevents silylation of the corresponding hydroxyl group (562−73+15=504).

This hypothesis was confirmed by testing the pharmacological activity of rosmanol.

C) TESTING THE PHARMACEUTICAL ACTIVITY OF ROSMANOL

The pharmacological activity of rosmanol is confirmed on the model of isolated hepatocytes poisoned with tert-butyl hydroperoxide. 25 mM of rosmanol completely inhibit the formation of malonaldehyde and reduce very significantly the necrotic effects.

The results showing the pharmacological activity of rosmanol are summarised in the table below:

|  | MAD | LDH | ASAT |
| --- | --- | --- | --- |
| DMSO | 0.31 ± 0.06 | 422 ± 72 | 29 ± 13 |
| tBH 1.5 mM | 6.82 ± 0.80 | 2428 ± 250 | 116 ± 15 |
| tBH + rosmanol 100 mM | 0.25 ± 0.05 | 268 ± 28 | 20 ± 1 |
| tBH + rosmanol 50 mM | 0.32 ± 0.06 | 350 ± 88 | 22 ± 2 |
| tBH + rosmanol 25 mM | 0.35 ± 0.08 | 434 ± 73 | 31 ± 2 |

We claim:

1. A pharmaceutical composition consisting essentially of, as the active substance, at least one of the compounds corresponding to formula I:

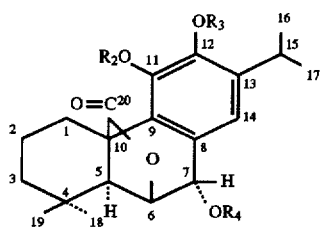

(I)

wherein $R_1$, $R_2$, $R_3$, which are identical or different, represent H, $CH_3$ or $C_2H_5$, optionally in association with a pharmaceutically acceptable salt.

2. A pharmaceutical composition according to claim 1, characterised in that it contains, as active substance, the compound corresponding to formula II:

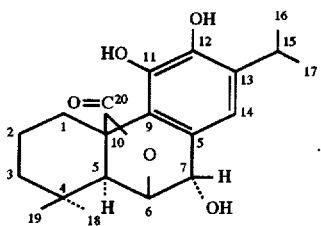

(II)

3. A pharmaceutical composition according to claim 2, characterised in that it contains about 0.1 mg/kg to about 100 mg/kg of active substance.

4. A pharmaceutical composition according to claim 3, characterised in that it contains about 1 mg/kg to about 10 mg/kg of active substance.

5. A pharmaceutical composition according to claim 1, characterised in that it contains, as active substance, the compound corresponding to formula III, IV or V:

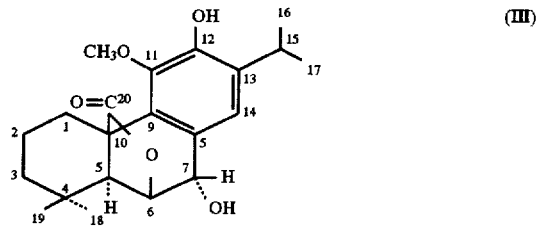

(III)

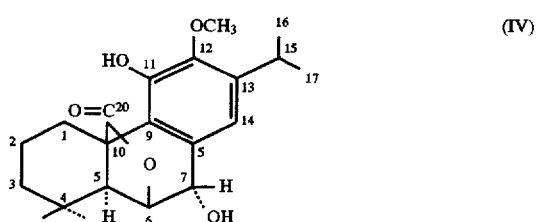

(IV)

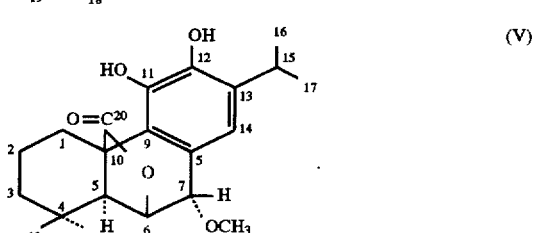

(V)

6. A pharmaceutical composition according to claim 5, characterised in that it contains about 0.1 mg/kg to about 100 mg/kg of active substance.

7. A pharmaceutical composition according to claim 6, characterised in that it contains about 1 mg/kg to about 10 mg/kg of active substance.

8. A pharmaceutical composition according to claim 1, characterised in that it contains, as active substance, the compound corresponding to formula VI, VII or VIII:

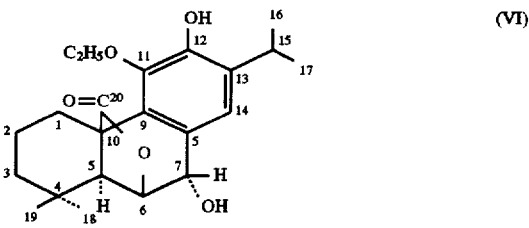

(VI)

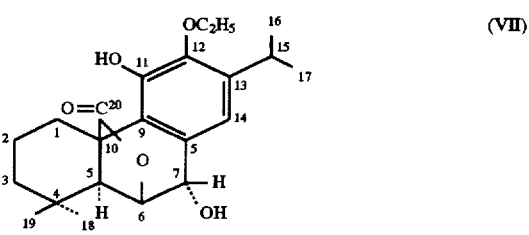

(VII)

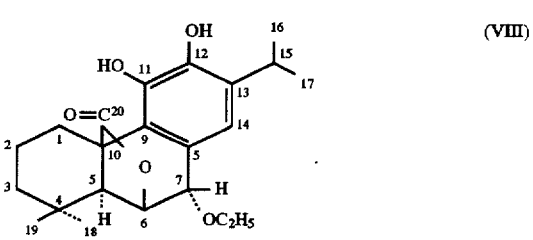

(VIII)

9. A pharmaceutical composition according to claim 8, characterised in that it contains about 0.1 mg/kg to about 100 mg/kg of active substance.

10. A pharmaceutical composition according to claim 9, characterised in that it contains about 1 mg/kg to about 10 mg/kg of active substance.

11. Pharmaceutical compositions having antiradical and/or antilipoperoxidative and/or hepatotropic properties and containing, as active substance, at least one of the compounds corresponding to formula I according to claim 1.

12. A pharmaceutical composition according to claim 1, characterised in that it contains about 0.1 mg/kg to about 100 mg/kg of active substance.

13. A pharmaceutical composition according to claim 12, characterised in that it contains about 1 mg/kg to about 10 mg/kg of active substance.

14. A pharmaceutical composition according to claim 1, characterised in that it is present in a form suitable for oral, parenteral, rectal or topical administration.

15. A pharmaceutical composition according to claim 1, characterised in that the active substance is derived from *Rosmatinus officinalis*.

16. Method for the treatment of pathologies associated with mechanisms of free radical formation or mechanisms of lipid peroxidation, which comprises administering a pharmaceutical composition having antiradical and/or antilipoperoxidative properties and containing from about 0.1 mg/kg to 100 mg/kg of an active substance comprised of at least one of the compounds corresponding to formula I:

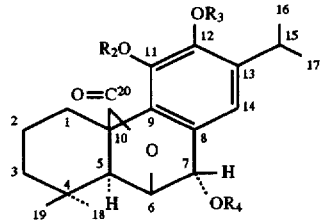

wherein $R_1$, $R_2$, $R_3$, which are identical or different, represent H, $CH_3$ or $C_2H_5$, optionally in association with a pharmaceutically acceptable salt.

17. Method for the treatment of the pathologies according to claim 16, wherein the pharmaceutical composition contains, as active substance, a compound corresponding to formula II:

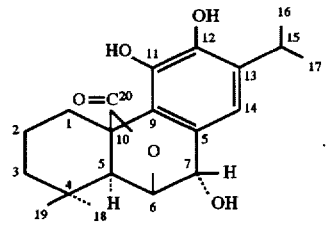

18. Method for the treatment of pathologies according to claim 16, wherein the pharmaceutical composition contains, as active substance, a compound corresponding to formula III, IV or V:

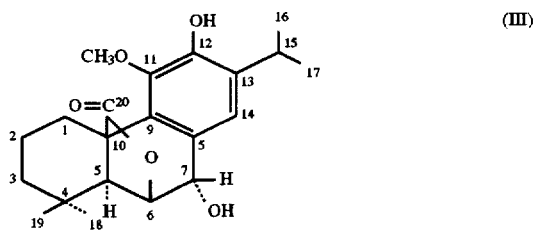

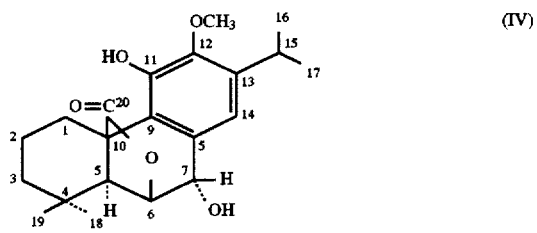

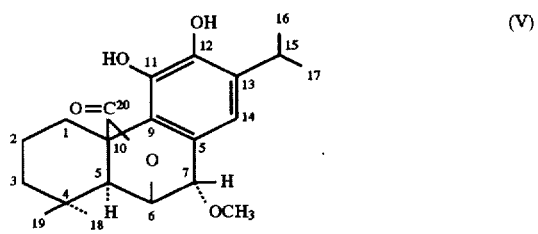

19. Method for the treatment of pathologies according to claim 16, wherein the pharmaceutical composition contains, as active substance, a compound corresponding to formula VI, VII or VIII:

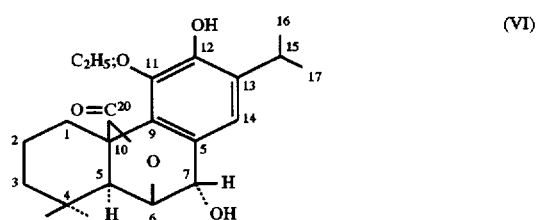

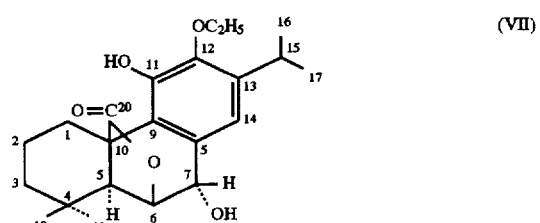

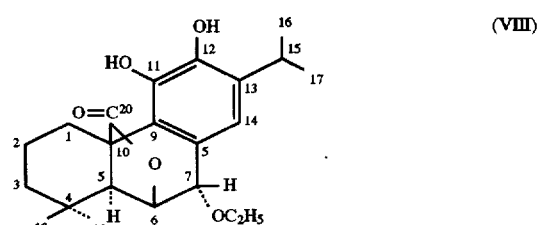

20. Method for the treatment of pathologies according to claim 16, wherein the pharmaceutical composition is administered orally, parenterally, rectally, or topically.

21. Method for the treatment of pathologies according to claim 16, wherein the pharmaceutical composition is in the form of one of tablets, dragees, capsules, powders, granules, suspensions, syrups, suppositories, solutions, eye washes and creams.

22. Method for the treatment or protection of hepatic cells from hepatic diseases of toxic origin, which comprises administering a pharmaceutical composition having hepatotropic properties and containing from about 1 mg/kg to 100 mg/kg of an active substance comprised of at least one of the compounds corresponding to formula I:

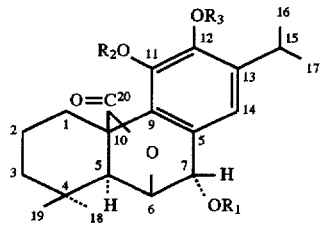
(I)

wherein $R_1$, $R_2$, $R_3$, which are identical or different, represent H, $CH_3$ or $C_2H_5$, optionally in association with a pharmaceutically acceptable salt.

23. Method for the treatment or protection of hepatic cells according to claim 22, wherein the pharmaceutical composition contains, as active substance, a compound corresponding to formula II:

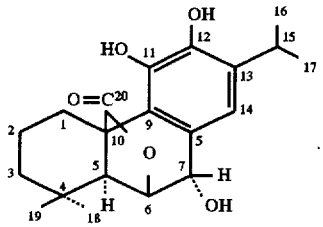
(II)

24. Method for the treatment or protection of hepatic cells according to claim 22, wherein the pharmaceutical composition contains, as active substance, a compound corresponding to formula III:

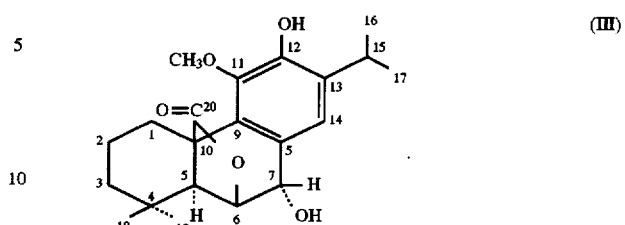
(III)

25. Method for the treatment or protection of hepatic cells according to claim 22, wherein the pharmaceutical composition contains, as active substance, a compound corresponding to formula IV:

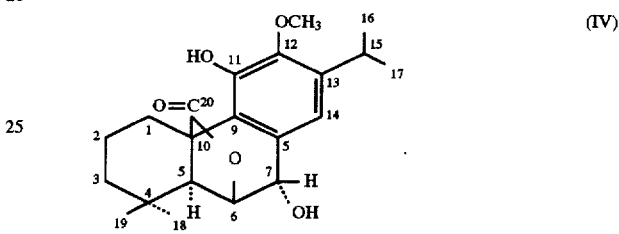
(IV)

* * * * *